United States Patent [19]

Rolf et al.

[11] Patent Number: 5,625,070

[45] Date of Patent: Apr. 29, 1997

[54] PREPARATION OF COTININE BY REACTING NICOTINE WITH BROMIDE AND BROMATE

[75] Inventors: David Rolf, Minneapolis; David J. W. Goon, Bloomington; Robert H. Michelson, Eagan, all of Minn.

[73] Assignee: Lectec Corporation, Minnetonka, Minn.

[21] Appl. No.: 481,769

[22] Filed: Jun. 7, 1995

[51] Int. Cl.⁶ .................. C07D 401/04; C07D 403/04
[52] U.S. Cl. ..................... 546/278.4; 546/279.4
[58] Field of Search ............... 546/278.4, 279.4

[56] References Cited

FOREIGN PATENT DOCUMENTS 51-105076A  9/1976  Japan ................... C07D 401/04

OTHER PUBLICATIONS

*Biochemical Preparations*, vol. 10, pp. 36–39; John Wiley & Sons, New York, 1963.
*Synthetic Communications*, 18(12) pp. 1331–1337 (1988).
Peeters et al., Journal of Labelled Compounds and Radiopharmaceuticals, vol. 27(5), pp. 605–611, May 1989.
Desai et al., Journal of Radiolabelled Compounds and Radiopharmaceuticals, vol. 29, (3) Mar. 1991.

*Primary Examiner*—Alan L. Rotman
*Attorney, Agent, or Firm*—James V. Harmon

[57] ABSTRACT

Cotinine is prepared from nicotine or nicotine sulfate by mixing a solution thereof with compounds having the formula $XBr$, $YBrO_3$ where X is hydrogen or an alkali metal and Y is an alkali metal to produce an intermediate product: dibromocotinine hydrobromide perbromide, which is reduced and de-brominated to produce cotinine.

11 Claims, 1 Drawing Sheet

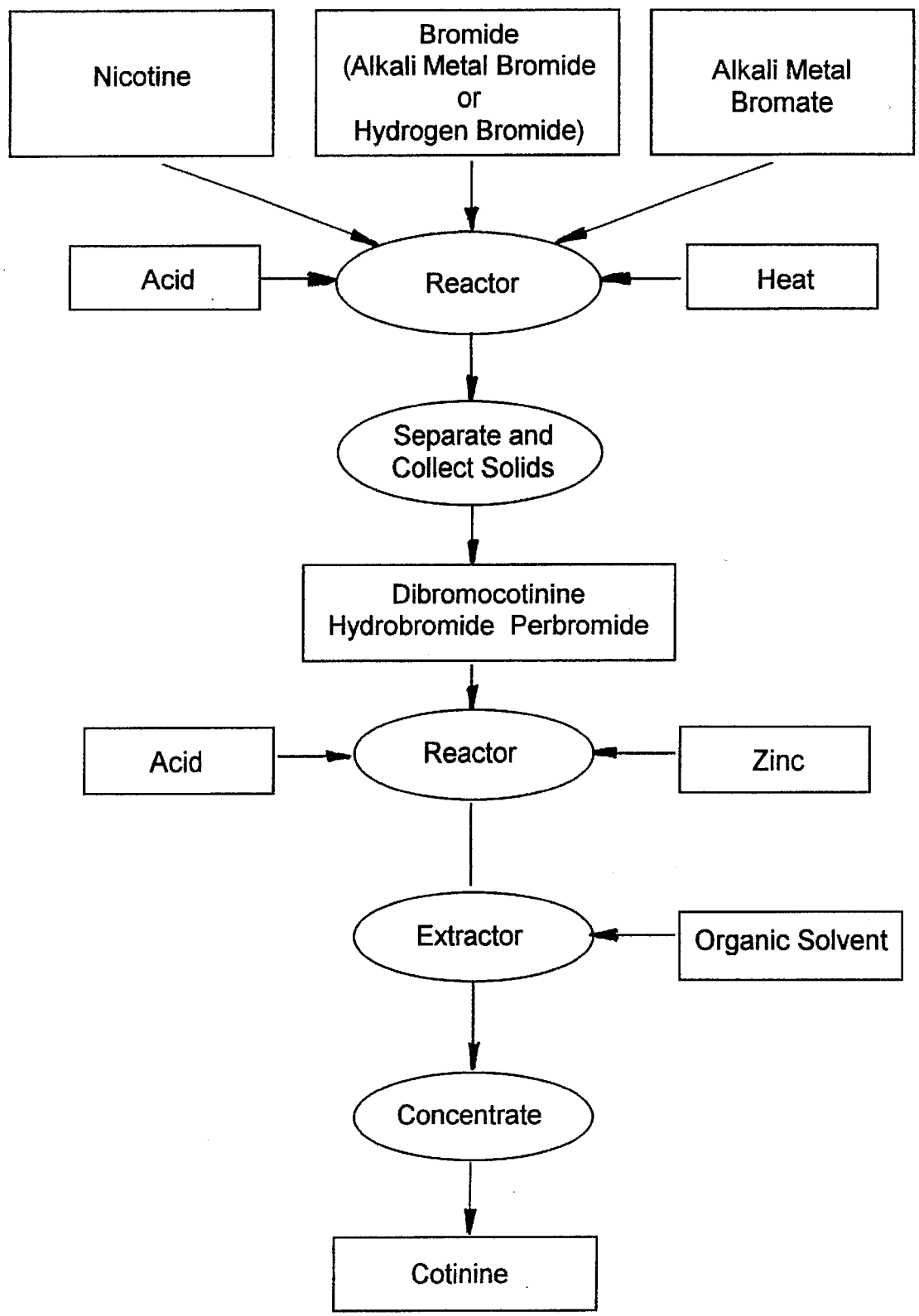

PREPARATION OF COTININE BY REACTING NICOTINE WITH BROMIDE AND BROMATE

FIELD OF THE INVENTION

This invention relates to the production of cotinine from nicotine.

BACKGROUND OF THE INVENTION

Cotinine has been synthesized by reacting bromine with nicotine to form an intermediate, dibromocotinine hydrobromide perbromide, which is then reduced by the addition of zinc and hydrochloric acid to yield cotinine (*Biochemical Preparations*, Vol. 10, pp. 36–39). Japanese patent JP51105076A dated Sep. 17, 1976 describes another method wherein nicotine is reacted with hydrobromic acid and hydrogen peroxide to produce the intermediate which is reduced and debrominated by the usual method without isolation. In another method, cotinine was produced by oxidizing nicotine with a Hg(II)-EDTA complex (*Synthetic Communications*, 18(12), pp. 1331–1337; 1988). A major object of the present invention is to avoid the use of toxic substances such as bromine, mercury and to avoid the combined use of hydrobromic acid and hydrogen peroxide as described in JP 51105076A because of the expense of HBr and because the yield of cotinine was found by us to be relatively poor. The use of toxic materials is particularly objectionable where the final product is to be formed without physical separation from the intermediate. In addition, safety problems are incurred and manufacturing costs are increased because of the special handling and treatment required for the toxic substances previously required.

Accordingly, it is a major object of the present invention to provide an improved commercial method for producing cotinine in high yields and on a commercial scale without the drawback produced by the toxicity problems, poor yields, and costly reagents needed in previous methods.

These and other more detailed and specific objects of the present invention will be better understood by reference to the following figures and detailed description which illustrate by way of example but a few of the various forms of the invention within the scope of the appended claims.

SUMMARY OF THE INVENTION

Briefly, in accordance with the method of the present invention, cotinine is prepared from nicotine or nicotine sulfate by mixing a solution thereof with compounds having the formula XBr, YBrO$_3$ where X is an alkali metal or hydrogen and Y is an alkali metal to produce an intermediate product: dibromocotinine hydrobromide perbromide, which is reduced and de-brominated to produce cotinine. Cotinine has utility in reducing tension and anxiety, appetite suppression, treating inflammatory bowel, and alleviating tobacco withdrawal (see co-pending application Ser. Nos. 07/885,314, 07/964,227 and 08/124,004).

Additional features of the invention will be apparent from consideration of the accompanying specification, claims and drawings which illustrate by way of example but a few of the various ways in which the invention can be accomplished.

THE FIGURE

The FIGURE is a flow diagram illustrating an example of the invention.

DETAILED DESCRIPTION OF THE INVENTION

In accordance with the present invention, nicotine is reacted with an alkali metal bromide or hydrobromic acid (hydrogen bromide) and an alkali metal bromate in the manufacture of cotinine. In accordance with this improved method, nicotine or nicotine sulfate (hereinafter referred to simply as "nicotine") is reacted with the bromide salt, e.g., sodium bromide or potassium bromide and/or hydrobromic acid, and an alkali metal bromate under acid conditions to produce an intermediate, dibromocotinine hydrobromide perbromide. The intermediate is then reduced and de-brominated following the general approach of McKennis and Bowman (*Biochemical Preparations*, Vol. 10, pp. 36–39) to produce cotinine. However, unlike the method of Bowman and McKennis, it is not necessary to isolate the intermediate. Consequently, the reaction can be carried out in a sequential manner in the same reactor. Zinc dust or granules may be added after the intermediate has precipitated, even without the addition of an acid such as hydrochloric acid.

The invention will be better understood by reference to the FIGURE which illustrates the invention by way of example. As shown in the FIGURE, nicotine together with an alkali metal bromide, e.g., sodium bromide or hydrogen bromide, and an alkali metal bromate, e.g., sodium bromate, was placed in an aqueous solution in a reactor and heated in the presence of an acid, e.g., hydrochloric and acetic acids. The red color produced in the reactor indicated the presence of elemental bromine. A red-orange precipitate of dibromocotinine hydrobromide perbromide was then separated and collected by suction filtration. This intermediate product was then kept in the same reactor or, if desired, isolated and placed in a second reactor. The intermediate product is mixed with an acid, e.g., acetic acid and hydrochloric acid, followed by the addition of zinc dust or granules. The zinc was removed by suction filtration and the resulting cotinine was extracted with an organic solvent, e.g., chloroform. Finally, the extract was concentrated by evaporation to produce cotinine as a brown, viscous liquid. Analysis by thin-layer chromatography (TLC) showed that the material collected was about 95% cotinine with norcotinine as a by-product with a trace of nicotine present.

The invention involves the in situ generation of bromine from bromide and bromate ions under acidic conditions according to the following equation:

$$5Br^- + BrO_3^- + 6H^+ \rightarrow 3Br_2 + 3H_2O$$

The storage and handling of bromine which is both expensive and hazardous is circumvented in the present invention. The invention also makes it possible to eliminate the use of hydrobromic acid (HBr) which is relatively expensive. The bromide and bromate ions can be provided from relatively inexpensive sources such as potassium and sodium salts which are the most economical. The invention also takes advantage of using hydrochloric and/or sulfuric acid which are both relatively inexpensive. The most economical and preferred combination of reagents to be used in the present invention are sodium bromide, sodium bromate, and hydrochloric acid or sulphuric acid.

The use of zinc dust or granules with hydrochloric acid is the preferred method of reducing the intermediate to cotinine. This can be done without isolating the intermediate. Even if the intermediate is not isolated, the reduction reaction proceeds readily and the cost of the reagents is low.

The cotinine that is collected from the organic solvent can be purified readily by performing vacuum distillation, preferably using a silvered vacuum-jacketed column such as a Vigreux column.

The invention will be better understood by reference to the following examples. All quantities given herein are expressed as percent (%) or parts by weight, as indicated.

EXAMPLE 1

In a 3-neck round bottom flask fitted with mechanical stirrer and thermocouple digital thermometer was added water (350 mL) and sodium bromide (321.0 g, 3.12 mol). After stirring for 10 minutes the sodium bromide dissolved. Nicotine (50.5 g, 0.311 mol) followed by concentrated hydrochloric acid (312 mL, 3.74 mol) were then added. White solids that appeared to be NaBr/NaCl precipitated and a solution of sodium bromate (94.1 g, 0.164 mol) in water (300 mL) was added over 15 minutes. The red color of bromine formed immediately, and the reaction temperature rose from 35° C. to 44° C. Water (500 mL) was added, and the reaction was stirred and heated with a heating mantle at 78°–84° C. for 4 hours. Glacial acetic acid (200 mL) was added and the reaction was stirred overnight at room temperature. Red-orange solids started forming soon after the addition of the acetic acid, and the next day these solids were collected by suction filtration and washed with cold water (500 mL). After partial drying with a water aspirator, the solids (158 g) were suspended into 50% aqueous acetic acid (500 mL). The reaction flask was cooled in an ice bath while concentrated hydrochloric acid (65 mL) was added all at once followed by zinc dust (126.0 g, 1.93 mol) in small portions over 10 minutes. The reaction temperature reached 50° C. but after the initial addition of zinc, the temperature remained below 40° C. After stirring for 40 minutes, concentrated ammonium hydroxide was added (pH 8.5), and the reaction was stirred for 1.5 hours. Zinc and zinc salts were removed by suction filtration with a Büchner funnel, and the filtrate was extracted with chloroform (4×500 mL). The extract was dried (sodium sulfate) and concentrated on a rotary evaporator to give 46.2 g (84.3% yield) of brown, viscous liquid. Analysis by thin-layer chromatography (TLC) (silica gel GF; chloroform:methanol:glacial acetic acid, 60:10:1, visualization by ultraviolet light (254 nm) and iodine) showed the major spot to be cotinine with norcotinine as a by-product and a trace of nicotine present. High pressure liquid chromatography (HPLC) showed <5% norcotinine.

To the filtrate of the orange solids (pH <3) was added zinc dust (63.0 g, 0.964 mol) and concentrated hydrochloric acid (25 mL). The reaction was stirred for 0.5 hour when concentrated ammonium hydroxide (350 mL) was added (pH 8.5). After 0.5 hour of stirring, the reaction was filtered, and the filtrate was divided into two equal portions. Each portion was extracted with methylene chloride (3×250 mL). Workup as above gave another 8.2 g (total yield 54.4 g, 99.3% yield) of brown liquid which was by TLC mainly cotinine (>95%) with norcotinine present but no nicotine was observed.

Cotinine is separated from nicotine and norcotinine by vacuum distillation using a silvered, vacuum jacketed Vigreux column.

EXAMPLE 2

The apparatus was the same as in Example 1. To nicotine (50.5 g, 0.311 mol) water (400 mL) and concentrated HBr (462 mL) was added over 40 minutes a solution of NaBrO$_3$ (108.6 g, 0.720 mol) and water (350 mL). Initially, cloudiness appeared at the point of contact, and half-way through the addition it was apparent bromine had formed. Water (500 mL) was added and the reaction was stirred and heated at 70°–85° C. for 2 hours. The reaction was stirred at room temperature overnight. The red-brown solids which had formed were collected by suction filtration, washed with cold water (300 mL), and partially dried by water aspirator to give 210.9 g of solids. These solids were suspended into water (500 mL) and concentrated HCl (65 mL) was added. The reaction was cooled in an ice bath and with stirring Zn dust (175.0 g, 2.67 mol) was added over 15 minutes. After stirring for 15 minutes, concentrated NH$_4$OH (300 mL) was added (pH 9). After 15 minutes of stirring, the reaction was worked up as Example 1 to yield 44.3 g (80.8% yield) of brown liquid. TLC analysis showed this liquid to be mainly cotinine with some norcotinine present. HPLC analysis showed <1% norcotinine. Use of HBr is not as economical as the reagents in Example 1.

EXAMPLE 3

Nicotine (50.5 g, 0.311 mol), 80% aqueous acetic acid (300 mL), and concentrated HBr (450 mL, 4.05 mol) were added in that order to the reaction flask followed by the addition of a solution of NaBrO$_3$ (93.1 g, 0.617 mol) in water (350 mL) over 15 minutes. The reaction was stirred and heated at 79°–81° C. for 3 hours. After stirring at room temperature overnight, the orange powdery solids that had formed were collected, washed with ice-cooled water (250 mL), and partially dried by water aspiration to give 213.8 g. These solids were suspended into 50% aqueous acetic acid (500 mL), concentrated HCl (65 mL) was added, the reaction was cooled in an ice bath, and with stirring zinc dust (175.0 g, 2.67 mol) was added over 15 minutes. After stirring for 0.5 hour, concentrated NH$_4$OH (400 mL) was added to bring the pH to 8.5–9. The reaction was worked up as in Example 1 to give 43.7 g (79.7% yield). TLC analysis showed mostly cotinine with some norcotinine and a trace amount of nicotine present. HPLC analysis showed <2% norcotinine.

EXAMPLE 4

Nicotine (50.5 g, 0.311 mol), glacial acetic acid (200 mL), and concentrated HBr (484 mL, 4.36 mol) were added to the reaction flask followed by a solution (at ~45° C.) of potassium bromate (104.1 g, 0.623 mol) in water (1 L) over 10 minutes. The reaction was stirred and heated at 85°–90° C. for 5 hours. Orange solids were present at the end of this time. The reaction was stirred at room temperature overnight and the solids were collected by suction filtration, washed with ice-cooled water (500 mL), and partially dried by water aspiration to give 141.4 g of granular, orange solids. The solids were suspended in water (500 mL), concentrated HCl (65 mL) was added, the reaction was cooled in an ice bath, and zinc dust (126.0 g, 1.93 mol) was added over 10 minutes. After stirring for 0.5 hour, concentrated NH$_4$OH (200 mL) was added (pH 9). After stirring for 0.5 hour, the solids were removed by air filtration. The filtrate was extracted with chloroform (4×250 mL), and the extract was worked up as in Example 1 to give 35.3 g (64.4% yield) of light yellow liquid. TLC analysis showed only the presence of cotinine. HPLC analysis showed <1% norcotinine.

The filtrate of the orange solids was cooled in an ice bath and zinc dust (63.0 g, 0.964 mol) was added over 5 minutes. After stirring for 0.5 hour, concentrated NH$_4$OH (400 mL) was added (pH 8.5). After stirring for 1 hour, the solids were removed by filtration, and the filtrate was divided into two equal portions. Each portion was extracted with chloroform (3×250 mL). Workup of the combined extracts gave 7.36 g (total 42.6 g, 77.7% yield). TLC analysis showed the presence of norcotinine and a trace of nicotine present. HPLC analysis showed 18% norcotinine present.

EXAMPLE 5

A solution of KBr (370.9 g, 3.12 mol) in water (500 mL), nicotine (50.5 g, 0.311 mol) and glacial acetic acid (200 mL) were added to the reaction flask. A white, filmy material formed. Concentrated HCl (312 mL, 3.74 mol) was added and white solids formed. A warm (38° C.) solution of KBrO₃ (104.1 g, 0.623 mol) and water (500 mL) was added over 10 minutes. The reaction turned red-orange in color immediately, and the reaction temperature rose to 44° C. The reaction was stirred and heated at 85°–90° C. for 5.5 hours (orange, granular solids present at this time) and then stirred at room temperature overnight. The solids were collected, washed with ice-cooled water, and partially dried by water aspiration to give 134.2 g. These solids were suspended into water (500 mL), and concentrated HCl (65 mL) was added. The reaction flask was cooled in an ice bath and zinc dust (126.0 g, 1.93 mol) was added over 15 minutes. After stirring for 1.5 hours, concentrated NH₄OH (200 mL) was added. After stirring for 0.5 hour, the solids were filtered off and the filtrate was extracted with chloroform (4×250 mL). Workup of the extract as in Example 1 gave 33.2 g (60.6% yield) of yellow liquid which TLC analysis showed to be mostly cotinine with some norcotinine but no nicotine present. HPLC analysis showed <2% norcotinine.

The filtrate of the orange solids was placed in the reaction flask which was then cooled by a water bath (~18° C.). Zinc dust (50.0 g, 0.765 mol) was added in 5 minutes. After stirring for 0.5 hour, concentrated NH₄OH (300 mL) was added. After stirring for 1 hour, the solids were removed by filtration, the filtrate was divided into two portions and each portion was extracted with methylene chloride (3×250 mL). The combined extracts were worked up in the usual way to give 10.5 g (total 43.7 g, 79.7% yield) of a brown, viscous liquid. TLC analysis showed a small amount of norcotinine (<5%) with a trace of nicotine present.

EXAMPLE 6

To a solution of NaBr (160.5 g, 1.56 mol) was added nicotine (25.3 g, 0.156 mol), glacial acetic acid (100 mL) and, with cooling in an ice bath, concentrated H₂SO₄ (104 mL, 1.87 mol). After the temperature had decreased to less than 30° C., a solution of NaBrO₃ (47.0 g, 0.312 mol) in water (150 mL) was added over 10 minutes. The reaction was heated and stirred at 81°–85° C. for 6 hours and stirred at room temperature overnight. Orange solids started to precipitate within the first hour of the latter. The reaction was cooled in an ice bath and zinc dust (63.0 g, 0.964 mol) was added over 15 minutes. After stirring for 0.5 hour, orange lumps were apparent in the mixture. The reaction was filtered, and the filtrate was worked up as in previous examples to give 13.69 g (49.8% of brown liquid).

The orange solids that had not reacted were manually removed from the zinc solids and suspended in water (150 mL). Glacial acetic acid (100 mL) and concentrated HCl (25 mL) were added. With cooling in an ice bath, zinc dust (30.0 g, 0.459 mol) was added over 10 minutes. The usual work up was followed to give 7.29 g of brown liquid (total 20.98 g, 76.3% yield). TLC analysis of the two isolated liquids showed norcotinine in both with very little or no nicotine present. HPLC analysis of the combined liquids showed 9% norcotinine.

EXAMPLE 7

Cotinine is produced as described in Example 6, except that NaBr is replaced by the following compounds in separate batches: Lithium bromide, rubidium bromide or cesium bromide and NaBrO₃ is replaced with lithium bromate, rubidium bromate or cesium bromate.

Many variations of the present invention within the scope of the appended claims will be apparent to those skilled in the art once the principles described herein are understood.

What is claimed is:

1. The process which comprises mixing a solution of a compound of the formula

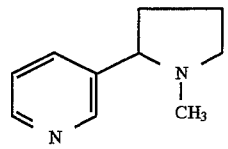

or a salt thereof, and a compound of the formula selected from the group consisting of XBr and YBrO₃ in which X is hydrogen or an alkali metal and Y is an alkali metal to produce an intermediate compound of the formula

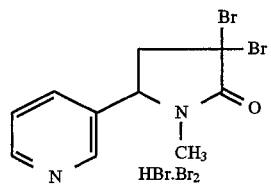

reducing and de-brominating said intermediate compound and recovering a product of the formula

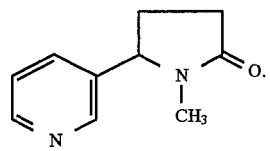

2. The process of claim 1 wherein XBr is at least one compound selected from the group consisting of HBr, NaBr, and KBr and an acid is added to said solution with said XBr and YBrO₃.

3. The process of claim 1 wherein YBrO₃ is at least one compound selected from the group consisting of NaBrO₃ and KBrO₃.

4. The process of claim 1 wherein said intermediate compound is reduced and de-brominated by reacting said intermediate with zinc in the presence of an acid selected from the group consisting of HCl and H₂SO₄.

5. The process of claim 4 wherein said intermediate compound is reacted with zinc in the presence of a weak acid.

6. The process of claim 5 wherein the weak acid is acetic acid.

7. The process of claim 4 wherein following the reaction of the intermediate compound with zinc, the acid is neutralized with a base and solids are collected by filtration, and the recovered cotinine is extracted with an organic solvent.

8. The process of claim 7 wherein the organic solvent is a chlorinated hydrocarbon.

9. The process of claim 2 wherein said acid is selected from the group consisting of HCl, H₂SO₄ and C₂H₄O₂.

10. The process of claim 1 wherein the recovered compound is extracted with a hydrocarbon.

11. The process of claim 10 wherein the hydrocarbon is a halogenated hydrocarbon.

* * * * *